(12) United States Patent
Matsumoto et al.

(10) Patent No.: US 8,242,303 B2
(45) Date of Patent: Aug. 14, 2012

(54) METHOD OF PRODUCING OPTICALLY ACTIVE N-(HALOPROPYL) AMINO ACID DERIVATIVE

(75) Inventors: Jun Matsumoto, Kobe (JP); Toru Inoue, Kobe (JP)

(73) Assignee: Nagase & Co., Ltd., Osaka-shi (JP)

( * ) Notice: Subject to any disclaimer, the term of this patent is extended or adjusted under 35 U.S.C. 154(b) by 270 days.

(21) Appl. No.: 12/671,565

(22) PCT Filed: May 19, 2008

(86) PCT No.: PCT/JP2008/059603
§ 371 (c)(1),
(2), (4) Date: Feb. 1, 2010

(87) PCT Pub. No.: WO2009/016879
PCT Pub. Date: Feb. 5, 2009

(65) Prior Publication Data
US 2011/0190527 A1    Aug. 4, 2011

(30) Foreign Application Priority Data

Aug. 1, 2007 (JP) ................................ 2007-200783

(51) Int. Cl.
*C07C 229/00* (2006.01)
(52) U.S. Cl. ........................................ 560/172; 560/155
(58) Field of Classification Search .................. None
See application file for complete search history.

(56) References Cited

FOREIGN PATENT DOCUMENTS

| JP | 2005 82572 | 3/2005 |
|---|---|---|
| JP | 2005-82572 | 3/2005 |

OTHER PUBLICATIONS

Feldman et al., J. Org. Chem. 1986, 51, 3882-3890.*
Aladzheva et al., Russian Chemical Bulletin (2005), 54(11), 2635-2641.*
Database Casreact, Chemical Abstracts Service, Columbus, Ohio, citation for J. Org. Chem. 1986, 51, 3882-3890.*
O. V. Bykhovskaya, et al., "Synthesis of 1,2-azaphospholanes containing an amino acid fragment", Russian Chemical Bulletin, International Edition, vol. 54, No. 11, Nov. 2005, pp. 2642-2647.
Gmeiner, P. et al., "An Efficient and Practical Total Synthesis of (+)-Vincamine From L-Aspartic Acid", Journal of Organic Chemistry, vol. 55, No. 10, pp. 3068-3074 (1990).
Feldman, P. L. et al., "Synthesis of Optically Pure $\Delta^4$ Tetrahydroquinolinic Acids and Hexahydroindolo {2,3-a} quinolizines From L-Aspartic Acid. Racemization on the Route to Vindoline", Journal of Organic Chemistry, vol. 51, No. 20, pp. 3882-3890 (1986).
Whitten, J. P. et al., "Synthesis of 3 (S)—Phosphonoacetyl-2 ( R)—Piperidinecarboxylic Acid, A Conformationally-Restricted Glutamate Antagonist", Bioorganic & Medical Chemistry Letters, vol. I, No. 9, pp. 441-444 (1991).
Kawabata, T. et al., "Asymmetric Cyclization Via Memory of Chirality: A Concise Access to Cyclic Amino Acids With a Quaternary Stereocenter", Journal of The American Chemical Society, vol. 125, No. 43, pp. 13012-13013 (2003).

* cited by examiner

*Primary Examiner* — Karl J Puttlitz
(74) *Attorney, Agent, or Firm* — Oblon, Spivak, McClelland, Maier & Neustadt, L.L.P.

(57) ABSTRACT

The present invention provides a method for producing an optically active N-(halopropyl)amino acid derivative, wherein the method comprises the steps of obtaining a compound represented by formula (III) by reacting an optically active alanine ester represented by formula (I) or a salt thereof (hereinafter sometimes simply referred to as an "alanine ester") with a halogenated propane represented by formula (II); and obtaining an optically active N-(halopropyl)amino acid derivative represented by formula (IV) by introducing a protecting group onto the nitrogen atom of the compound represented by formula (III). The present invention provides a method for efficiently producing an optically active N-(halopropyl)amino acid derivative.

14 Claims, No Drawings

METHOD OF PRODUCING OPTICALLY ACTIVE N-(HALOPROPYL) AMINO ACID DERIVATIVE

TECHNICAL FIELD

The present invention relates to a method for producing an optically active N-(halopropyl)amino acid derivative.

BACKGROUND ART

Optically active N-(halopropyl)amino acid derivatives are used for, for example, synthesizing optically active cyclic amino acids that are of use as synthetic intermediates of medicines, agrochemicals, and the like.

For such a method for synthesizing an optically active N-(halopropyl)amino acid derivative, Japanese Laid-Open Patent Publication No. 2005-82572 and T. Kawabata et al., "Journal of the American Chemical Society (J. Am. Chem. Soc.)", 2003, Vol. 125, pp. 13012-13013 disclose a method in which an optically active amino acid derivative and a halogenated alcohol (specifically, bromopropanol) are reacted to give an optically active N-(hydroxypropyl)amino acid derivative, the nitrogen atom of the obtained compound is protected by introducing a protecting group, and then the hydroxyl group is substituted with a halogen atom.

O. V. Bykhovskaya et al., "Russian Chemical Bulletin, International Edition", November 2005, Vol. 54, pp. 2642-2647 discloses a method for synthesizing a racemic N-(3-chloropropyl)alanine ethyl ester from ethyl bromoacetate and 3-chloropropylamine hydrochloride. This allows an N-(halopropyl)amino acid derivative to be produced.

However, the methods of Japanese Laid-Open Patent Publication No. 2005-82572 and T. Kawabata et al., "Journal of the American Chemical Society (J. Am. Chem. Soc.)", 2003, Vol. 125, pp. 13012-13013 use expensive bromopropanol as a starting material and require a step of substituting a hydroxyl group with a halogen atom. Furthermore, in order to use the obtained N-(hydroxypropyl)amino acid derivative as an intermediate in a subsequent step, a purification step with column chromatography or the like is also necessary. Moreover, since the N-(3-chloropropyl)alanine ethyl ester obtained according to the method disclosed in O. V. Bykhovskaya et al., "Russian Chemical Bulletin, International Edition", November 2005, Vol. 54, pp. 2642-2647 is a racemate, a step of optical resolution is necessary to obtain an optically active form thereof. Further, even if an acetate, which is a starting material, is processed in advance into its optically active form, it is not clear whether the optical activity is maintained after the reaction with an amine salt.

DISCLOSURE OF INVENTION

It is an object of the present invention to provide a method for efficiently producing an optically active N-(halopropyl) amino acid derivative.

The present invention provides a method for producing an optically active N-(halopropyl)amino acid derivative, wherein the method comprises the steps of: obtaining a compound represented by formula (III):

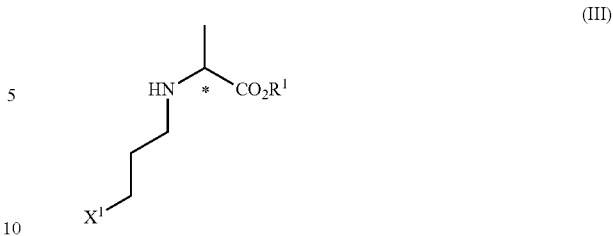

by reacting an optically active alanine ester represented by formula (I);

or a salt thereof with a halogenated propane represented by formula (II):

and obtaining an optically active N-(halopropyl)amino acid derivative represented by formula (IV);

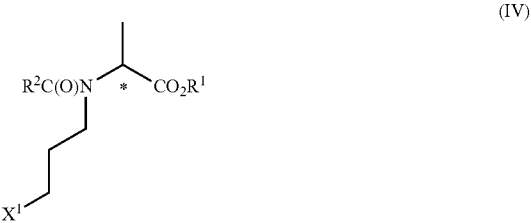

by introducing a protecting group onto the nitrogen atom of the compound represented by formula (III), wherein, in the compounds represented by formula (I), formula (II), formula (III), and formula (IV), $X^1$ and $X^2$ are different from each other and are atoms selected from the group consisting of a chlorine atom, a bromine atom, and an iodine atom, $X^2$ is an atom that has an atomic number larger than that of $X^1$, $R^1$ is a linear or branched alkyl group having 1 to 4 carbon atoms that may be substituted with a phenyl group or is a p-nitrophenyl group, $R^2$ is a phenyl group, a methyl group, a tert-butyl group, a tert-butoxy group, a benzyloxy group, a methoxy group, or a 9-fluorenylmethoxy group, and the asterisk (*) indicates an asymmetric carbon atom.

In one embodiment, in the compounds represented by formula (II), formula (III), and formula (IV), $X^1$ is a chlorine atom and $X^2$ is a bromine atom.

In one embodiment, the halogenated propane represented by formula (II) is used in a ratio of 1.5 to 4.5 equivalents relative to an amount of the optically active alanine ester represented by formula (I) or the salt thereof.

In one embodiment, in the optically active alanine ester represented by formula (I), $R^1$ is an unsubstituted linear alkyl group having 1 to 4 carbon atoms.

According to the method of the present invention, an optically active N-(halopropyl)amino acid derivative can be inexpensively and efficiently produced without requiring a step of substituting a halogen atom for the hydroxyl group derived from the bromopropanol used as a starting material, which is required in conventional methods, by using a halogenated propane represented by formula (II) as a starting material.

BEST MODE FOR CARRYING OUT THE INVENTION

The method for producing an optically active N-(halopropyl)amino acid derivative of the present invention includes the steps of obtaining a compound represented by formula (III) by reacting an optically active alanine ester represented by formula (I) or a salt thereof (hereinafter sometimes simply referred to as an "alanine ester") with a halogenated propane represented by formula (II); and obtaining an optically active N-(halopropyl)amino acid derivative represented by formula (IV) by introducing a protecting group onto the nitrogen atom of the compound represented by formula (III). The present invention will be described below in detail.

The optically active alanine ester used in the production method of the present invention is represented by formula (I).

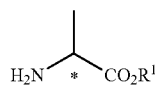

(I)

In formula (I), $R^1$ is a linear or branched alkyl group having 1 to 4 carbon atoms that may be substituted with a phenyl group or is a p-nitrophenyl group. Preferably, $R^1$ is an unsubstituted, linear or branched alkyl group having 1 to 4 carbon atoms, and more preferably an unsubstituted, linear alkyl group having 1 to 4 carbon atoms. Specific examples of linear or branched alkyl groups having 1 to 4 carbon atoms that may be substituted with a phenyl group include a methyl group, an ethyl group, a benzyl group, an isopropyl group, a tert-butyl group, and the like.

Examples of salts of the optically active alanine ester represented by formula (I) include, but are not limited to, hydrochloride, sulfate, p-toluenesulfonate (tosylate), and the like.

Commercially available products may be used for such alanine esters (for example, hydrochloride and tosylate are commercially available from Bachem) and such alanine esters may be synthesized for use. Moreover, an alanine ester may be either the L isomer or the D isomer. The optically active alanine ester used in the present invention has an optical purity of preferably 95% ee or more, more preferably 98% ee or more, and still more preferably 99% ee or more. Among the optically active alanine ester or a salt thereof, the hydrochloride and the tosylate of an optically active alanine ester are preferably used in terms of availability, and the hydrochloride of an optically active alanine ethyl ester is used more preferably.

The halogenated propane used in the production method of the present invention is represented by formula (II).

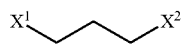

(II)

In formula (II), $X^1$ and $X^2$ are different from each other and are atoms selected from the group consisting of a chlorine atom, a bromine atom, and an iodine atom. Moreover, $X^2$ is an atom that has an atomic number larger than that of $X^1$. That is, $X^2$ is an atom that is more reactive than $X^1$ relative to the alanine ester. Combinations of such $X^1$ and $X^2$ include a bromine atom ($X^2$, atomic number: 35) and a chlorine atom ($X^1$, atomic number: 17); an iodine atom ($X^2$, atomic number: 53) and a bromine atom ($X^1$, atomic number: 35); and an iodine atom ($X^2$, atomic number: 53) and a chlorine atom ($X^1$, atomic number: 17). Among these combinations, a combination of a bromine atom ($X^2$, atomic number: 35) and a chlorine atom ($X^1$, atomic number: 17) is preferable. In the case of this combination, the compound represented by formula (III) that is obtained from the alanine ester and the halogenated propane represented by formula (II) offers a significantly reduced possibility of undergoing a side reaction due to the terminal halogen atom $X^1$.

Examples of halogenated propanes represented by formula (II) include 1-bromo-3-chloropropane, 1-chloro-3-iodopropane, and 1-bromo-3-iodopropane. Among these examples, 1-bromo-3-chloropropane (i.e., a combination of a bromine atom ($X^2$) and a chlorine atom ($X^1$)) is used preferably.

In the production method of the present invention, the amounts of the alanine ester and the amounts of the halogenated propane represented by formula (II) are not particularly limited. Relative to the amount of the alanine ester, the halogenated propane represented by formula (II) is usually used in a ratio of 0.5 to 10 equivalents, preferably 0.8 to 7 equivalents, and more preferably 1.5 to 4.5 equivalents. In particular, when $X^1$ and $X^2$ of the halogenated propane represented by formula (II) are a chlorine atom ($X^1$) and a bromine atom ($X^2$), respectively (i.e., 1-bromo-3-chloropropane), the halogenated propane is preferably used in a ratio of 1.5 to 4.5 equivalents.

Usually, the reaction is carried out in an inert solvent (that is, a solvent inert to the optically active alanine ester represented by formula (I) or a salt thereof and to the halogenated propane represented by formula (II) used in the present invention). The inert solvent is not particularly limited. Preferable examples of such solvents include aromatic hydrocarbons such as benzene, toluene, xylene, and mesitylene; ethers such as diethyl ether, diisopropyl ether, tetrahydrofuran, dioxane, cyclopentyl methyl ether, and methyl tert-butyl ether; esters such as ethyl acetate and isopropyl acetate; nitriles such as acetonitrile and chloroacetonitrile; aprotic polar solvents such as dimethylformamide and dimethylacetamide; and halogenic solvents such as dichloromethane and dichloroethane. Acetonitrile, dimethylformamide, and toluene are used more preferably.

The reaction temperature and the reaction time can be suitably determined according to, for example, the halogenated propane used and the type of solvent. The reaction temperature may be preferably 0 to 150° C., and more preferably 20 to 100° C. The reaction time may be preferably 0.5 to 36 hours, and more preferably 1 to 18 hours.

Furthermore, the reaction may be carried out in the presence of a base. The base to be used is not particularly limited, and examples include organic bases such as triethylamine and diisopropylethylamine; and inorganic bases such as potassium carbonate, sodium hydrogencarbonate, and sodium carbonate. Further, in order to promote the reaction, iodine compounds such as sodium iodide and potassium iodide may be added as an additive.

In this manner, a compound represented by formula (III) is obtained.

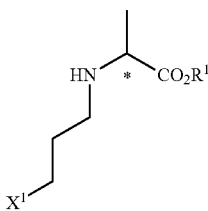
(III)

In formula (III), the asterisk (*) indicates an asymmetric carbon atom and $X^1$ is a chlorine atom or a bromine atom. $X^1$ is identical to $X^1$ of the halogenated propane represented by formula (II).

Examples of compounds represented by formula (III) include the R isomer or S isomer of N-(3-chloropropyl)alanine ethyl ester, the R isomer or S isomer of N-(3-bromopropyl)alanine ethyl ester, the R isomer or S isomer of N-(3-chloropropyl)alanine methyl ester, the R isomer or S isomer of N-(3-bromopropyl)alanine methyl ester, the R isomer or S isomer of N-(3-chloropropyl)alanine isopropyl ester, the R isomer or S isomer of N-(3-bromopropyl)alanine isopropyl ester, the R isomer or S isomer of N-(3-chloropropyl)alanine tert-butyl ester, the R isomer or S isomer of N-(3-bromopropyl)alanine tert-butyl ester, the R isomer or S isomer of N-(3-chloropropyl)alanine benzyl ester, the R isomer or S isomer of N-(3-bromopropyl)alanine benzyl ester, the R isomer or S isomer of N-(3-chloropropyl)alanine p-nitrophenyl ester, the R isomer or S isomer of N-(3-bromopropyl)alanine p-nitrophenyl ester, and the like. In the method of the present invention, a compound represented by formula (III) can be obtained while maintaining the asymmetry of the optically active alanine ester, that is, while maintaining the spatial configuration between the asymmetric carbon atom and the surrounding atoms or atomic groups that are bonded to the asymmetric carbon atom within the optically active alanine ester.

Then, by introducing a protecting group onto the nitrogen atom of the compound represented by formula (III), an optically active N-(halopropyl)amino acid derivative represented by formula (IV) (hereinafter sometimes simply referred to as an "amino acid derivative") is obtained. Here, a protecting group means a group that is temporarily used to protect a highly reactive group when a reaction of such a highly reactive group such as an amino group (—NH₂, —NH—, or the like) present within the molecule needs to be prevented while another moiety within the molecule needs to be reacted. The protecting group is removed after the reaction to recover the original high reactive group such as an amino group (—NH₂, —NH—, or the like).

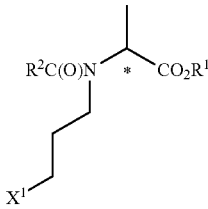
(IV)

In formula (IV), the asterisk (*) indicates an asymmetric carbon atom and $X^1$ is a chlorine atom or a bromine atom. $X^1$ is identical to $X^1$ of the halogenated propane represented by formula (II).

In formula (IV), $R^2C(O)$ indicates a protecting group, and $R^2$ is a phenyl group, a methyl group, a tert-butyl group, a tert-butoxy group, a benzyloxy group, a methoxy group, or a 9-fluorenylmethoxy group.

A protecting group may be introduced into the compound represented by formula (III) as it is, or a protecting group may be introduced after converting the compound into the form of a salt and purifying it. When a salt is formed, examples of acids to be used include hydrochloric acid, sulfuric acid, hydrobromic acid, acetic acid, toluenesulfonic acid, oxalic acid, and the like.

In the production method of the present invention, a method for introducing a protecting group is not particularly limited. For example, a solvent such as ethyl acetate is added to the compound represented by formula (III), and a reaction is carried out with excess acid chloride or acid anhydride in the presence of organic bases such as triethylamine and diisopropylethylamine. Alternatively, for example, when a protecting group is introduced into the hydrochloride of the compound represented by formula (III), a solvent such as ethyl acetate is added to the hydrochloride of the compound, and a reaction is carried out with excess acid chloride or acid anhydride in the presence of aqueous inorganic basic solution such as potassium carbonate, sodium hydrogencarbonate, and sodium carbonate.

Examples of acid chlorides used to introduce a protecting group include benzoyl chloride, benzyloxycarbonyl chloride, acetyl chloride, and the like. Examples of acid anhydrides include di-tert-butyl dicarbonate, acetic anhydride, and the like.

The reaction temperature and the reaction time for introducing a protecting group are suitably determined by a person skilled in the art. The reaction temperature may be preferably 0 to 50° C., and more preferably 5 to 30° C. Since the reaction time depends on the amounts of the compound represented by formula (III) and the acid chloride or acid anhydride (i.e., reaction scale), it is not necessarily specified. The reaction time may be preferably 0.5 to 48 hours, and more preferably 1 to 24 hours.

In this manner, a compound represented by formula (IV) into which a protecting group has been introduced is obtained. Examples of amino acid derivatives represented by formula (IV) include the R isomer or S isomer of N-(3-chloropropyl)-N-(tert-butoxycarbonyl)alanine ethyl ester, the R isomer or S isomer of N-(3-chloropropyl)-N-(pivaloyl) alanine ethyl ester, the R isomer or S isomer of N-(3-chloropropyl)-N-(benzyloxycarbonyl)alanine ethyl ester, the R isomer or S isomer of N-(3-chloropropyl)-N-(benzoyl)alanine ethyl ester, the R isomer or S isomer of N-(3-chloropropyl)-N-(methoxycarbonyl)alanine ethyl ester, the R isomer or S isomer of N-(3-chloropropyl)-N-(9-fluorenylmethoxycarbonyl)alanine ethyl ester, the R isomer or S isomer of N-(3-chloropropyl)-N-(acetyl)alanine ethyl ester, the R isomer or S isomer of N-(3-bromopropyl)-N-(tert-butoxycarbonyl)alanine ethyl ester, the R isomer or S isomer of N-(3-chloropropyl)-N-(tert-butoxycarbonyl)alanine methyl ester, the R isomer or S isomer of N-(3-chloropropyl)-N-(tert-butoxycarbonyl)alanine isopropyl ester, the R isomer or S isomer of N-(3-chloropropyl)-N-(tert-butoxycarbonyl)alanine tert-butyl ester, the R isomer or S isomer of N-(3-chloropropyl)-N-(tert-butoxycarbonyl)alanine benzyl ester, the R isomer or S isomer of N-(3-chloropropyl)-N-(tert-butoxycarbonyl)alanine p-nitrophenyl ester, and the like. In the method of the present invention, the compound represented by formula (IV) can be obtained while maintaining the asymmetry of the optically active alanine ester, that is, while maintaining the spatial configuration between the asymmetric carbon atom and the surrounding atoms or atomic groups that are bonded to the asymmetric carbon atom within the optically active alanine ester.

The N-(halopropyl)amino acid derivative obtained by the present invention has an optical purity of preferably 95% ee or more, more preferably 98% ee or more, and still more preferably 99% ee or more.

The amino acid derivative represented by formula (IV) can be used for the synthesis of optically active cyclic amino acids.

EXAMPLES

The present invention will be specifically described below by way of examples. However, the present invention is not limited to these examples.

The analytical conditions for gas chromatography (GC) used in the examples were as follows.

(GC Conditions)

Column: Shimadzu (CBP1 M-25) (25 m×0.25 mmφ)

Column temperature: from 50° C. (8 minutes) to 290° C., 15° C./min, retained for 3 minutes at 290° C.

Injector temperature: 250° C.

Detector temperature: 270° C.

Carrier gas: He, 1.3 mL/min

Split ratio: 1:100

Injector mode: Split

Sample amount: 1.0 µl

Detector: FID

Example 1

Synthesis of (R)—N-(3-chloropropyl)alanine ethyl ester hydrochloride

According to the reaction scheme below, the hydrochloride of (R)—N-(3-chloropropyl)alanine ethyl ester 3 (hereinafter sometimes simply referred to as the "hydrochloride 3") was obtained from D-alanine ethyl ester hydrochloride 1 and 1-bromo-3-chloropropane 2.

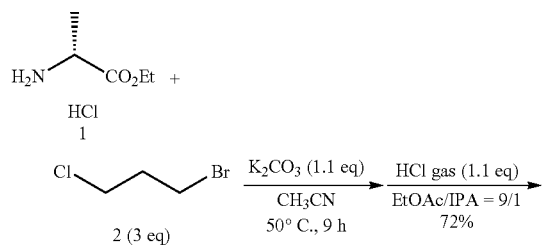

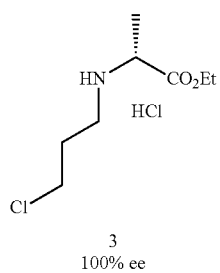

3
100% ee

Acetonitrile (380 mL), potassium carbonate (59.91 g; 0.419 mol), and 1-bromo-3-chloropropane 2 (180 g; 1.14 mol) were added to D-alanine ethyl ester hydrochloride 1 (58.54 g; 0.381 mol). A reaction was carried out while stirring at 50° C. for 9 hours. The reaction mixture was sampled, ethyl acetate and water were added thereto, the collected organic layer was analyzed by GC, and the reaction was finished after confirming that the peak derived from the D-alanine ethyl ester had disappeared (each peak in GC was: 1-bromo-3-chloropropane 2: 7.2 minutes, D-alanine ethyl ester: 7.4 minutes, and (R)—N-(3-chloropropyl)alanine ethyl ester: 16.1 minutes).

Then, the solvent (acetonitrile) was evaporated at 50° C. under a reduced pressure of 60 mmHg, 180 mL of ethyl acetate and 180 mL of water were added to the obtained residue, and an ethyl acetate layer was collected. To the remaining aqueous layer was added another 180 mL of ethyl acetate, and an ethyl acetate layer was collected. Then, the ethyl acetate layers were combined and washed twice with 90 mL of saturated brine.

After washing, 85 mL of an ethyl acetate solution containing 4.8 M hydrogen chloride gas and 53 mL of 2-propanol were added to the ethyl acetate layer, and stirring was performed at 60° C. for 30 minutes. After cooling, stirring was performed at 5° C. for 1 hour, and the precipitated solids were collected by filtration and washed with 150 mL of ethyl acetate, thereby giving the hydrochloride of (R)—N-(3-chloropropyl)alanine ethyl ester 3 (62.80 g; yield: 72%).

The results of GC analysis showed that the chemical purity of the resultant hydrochloride 3 was 97.1 Area % (analyzed after liberating the hydrochloride). The results of high performance liquid chromatography (HPLC) analysis showed an optical purity of 100% ee. The HPLC conditions were as follows. Note that the HPLC analysis was performed after liberating the hydrochloride 3 and benzoylating it according to the same method as in Example 3 below.

(HPLC Conditions)

Column: CHIRALCEL OD-H (4.6 mmφ×25 cm)

Mobile phase: hexane/2-propanol/diethylamine=97/3/0.1 (v/v/v)

Flow rate: 0.5 mL/min

Temperature: 40° C.

Detector: UV225 nm 33 minutes (R), 43 minutes (S)

The results of analysis of the resultant hydrochloride 3 were as follows.

Melting point: 162° C.

$^1$H-NMR (D$_2$O, 400 MHz) δ 4.41 (2H, q, J=7.2 Hz), 4.32-4.18 (1H, m), 3.85-3.75 (2H, m), 3.45-3.30 (2H, m), 2.35-2.20 (2H, m), 1.75-1.65 (3H, m), 1.40 (3H, t, J=7.2 Hz).

Example 2

Formation of tert-butoxycarbonyl of hydrochloride 3 (formation of Boc compound)

According to the reaction scheme below, the hydrochloride 3 obtained in Example 1 was converted into a Boc compound to introduce a protecting group onto the nitrogen atom.

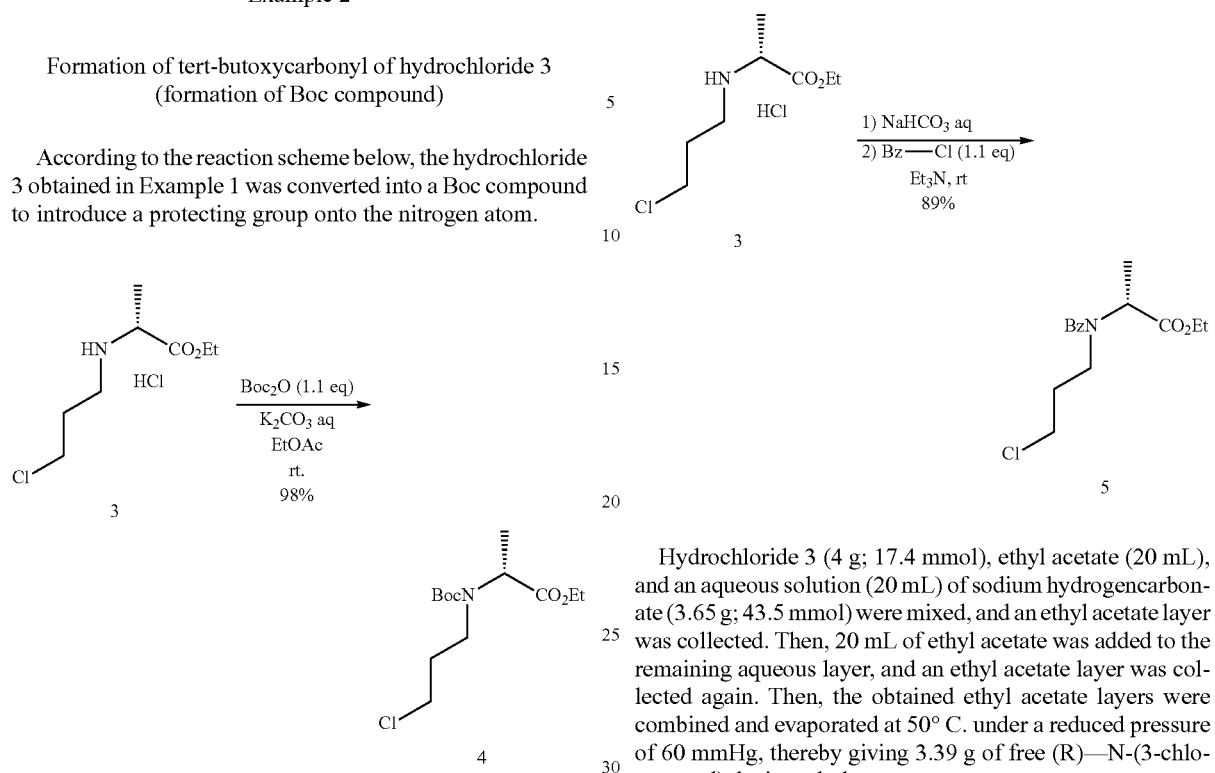

Ethyl acetate (200 mL) and an aqueous solution (220 mL) of potassium carbonate (22.5 g; 0.163 mol) were added to hydrochloride 3 (62.5 g; 0.272 mol).

Then, an ethyl acetate solution (70 mL) of di-tert-butyl dicarbonate ($Boc_2O$) (59.4 g; 0.272 mol) was added dropwise for 5 minutes, and then stirred at room temperature for 7 hours. The ethyl acetate layer in the reaction mixture was sampled and analyzed by GC, and the reaction was finished after confirming that the peak derived from (R)—N-(3-chloropropyl)alanine ethyl ester had disappeared (each peak in GC was: (R)—N-(3-chloropropyl)alanine ethyl ester: 16.1 minutes and (R)—N-(3-chloropropyl)-N-(tert-butoxycarbonyl)alanine ethyl ester 4: 20.0 minutes).

After the reaction was finished, the ethyl acetate layer was washed with 100 mL of 10% (w/v) aqueous citric acid solution and further washed with 200 mL of saturated brine. Then, ethyl acetate was evaporated at 50° C. under a reduced pressure of 60 mmHg, thereby giving crude (R)—N-(3-chloropropyl)-N-(tert-butoxycarbonyl)alanine ethyl ester 4 (78.7 g; yield: 98%) in the form of a colorless oil. The results of analysis of the resultant (R)—N-(3-chloropropyl)-N-(tert-butoxycarbonyl)alanine ethyl ester 4 were as follows.

$^1$H-NMR ($CDCl_3$, 400 MHz) δ 4.36-3.90 (1H, m), 4.17-4.09 (2H, m), 3.70-3.35 (3H, m), 3.30-3.10 (1H, m), 2.15-1.90 (2H, m), 1.53-1.26 (12H, m), 1.30-1.20 (3H, m)

Specific rotation $[α]_D^{20}$=40.0 (c 1.01, $CH_3OH$).

Example 3

According to the reaction scheme below, the hydrochloride 3 obtained in Example 1 was benzoylated to introduce a protecting group onto the nitrogen atom.

Hydrochloride 3 (4 g; 17.4 mmol), ethyl acetate (20 mL), and an aqueous solution (20 mL) of sodium hydrogencarbonate (3.65 g; 43.5 mmol) were mixed, and an ethyl acetate layer was collected. Then, 20 mL of ethyl acetate was added to the remaining aqueous layer, and an ethyl acetate layer was collected again. Then, the obtained ethyl acetate layers were combined and evaporated at 50° C. under a reduced pressure of 60 mmHg, thereby giving 3.39 g of free (R)—N-(3-chloropropyl)alanine ethyl ester.

Then, ethyl acetate (20 mL) and triethylamine (2.64 g; 26.1 mmol) were added to the resultant free (R)—N-(3-chloropropyl)alanine ethyl ester (3.39 g). Then, an ethyl acetate solution (20 mL) of benzoyl chloride (BzCl) (2.69 g, 19.1 mmol) was added dropwise for 15 minutes. Since solids precipitated when BzCl was added dropwise, another 20 mL of ethyl acetate was added to disperse the solids, and stirring was performed at room temperature for 0.5 hours. The ethyl acetate layer in the reaction mixture was sampled and analyzed by GC, and the reaction was finished after confirming that the peak derived from (R)—N-(3-chloropropyl)alanine ethyl ester had disappeared (each peak in GC was; (R)—N-(3-chloropropyl)alanine ethyl ester; 16.1 minutes, and (R)—N-(3-chloropropyl)-N-benzoylalanine ethyl ester 5: 23.2 minutes).

After the reaction was finished, another 20 mL of ethyl acetate was added. Then, the ethyl acetate layer was washed with 25 mL of a saturated aqueous sodium hydrogencarbonate solution and further washed with 25 mL of saturated brine. Then, ethyl acetate was evaporated at 50° C. under a reduced pressure of 60 mmHg, thereby giving a crude product in the form of a colorless oil (4.92 g). The obtained crude product was purified by silica gel column chromatography (silica gel 40 g, developing solvent: ethyl acetate/hexane=5/1 (v/v)), thereby giving (R)—N-(3-chloropropyl)-N-benzoylalanine ethyl ester 5 in the form of a colorless oil (4.55 g, yield: 89%). The results of analysis of the resultant (R)—N-(3-chloropropyl)-N-benzoylalanine ethyl ester 5 were as follows. Note that the optical purity of this (R)—N-(3-chloropropyl)-N-benzoylalanine ethyl ester 5 was 100% ee.

$^1$H-NMR ($CDCl_3$, 400 MHz) δ 7.50-7.30 (5H, m), 4.55-4.40 (1H, m), 4.20-4.00 (2H, m), 3.80-3.60 (2H, m), 3.55-3.30 (2H, m), 2.33-2.00 (2H, m), 1.60-1.40 (3H, m), 1.30-1.20 (3H, m)

Specific rotation $[α]_D^{20}$=70.6 (c 1.02, $CH_3OH$).

Example 4

According to the reaction scheme below, the hydrochloride 3 obtained in Example 1 was benzyloxycarbonylated (formation of Cbz compound) to introduce a protecting group onto the nitrogen atom.

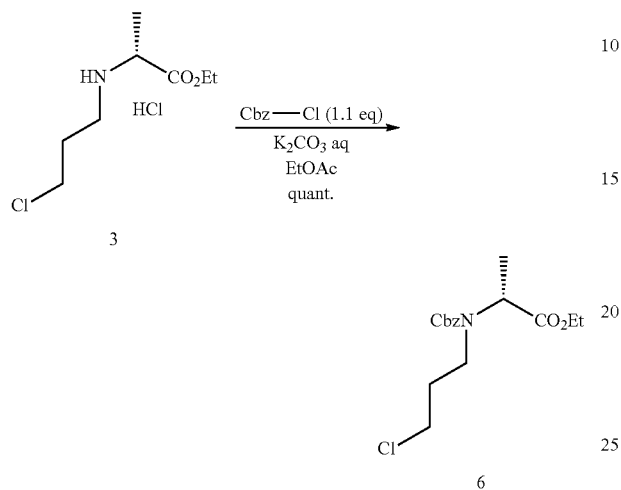

Hydrochloride 3 (1 g; 4.35 mmol) was dissolved in water (10 mL). Then, potassium carbonate (0.66 g; 4.78 mmol) and ethyl acetate (5 mL) were added.

Then, the mixture was cooled to 10° C. or below, an ethyl acetate solution (3 mL) of benzyloxycarbonyl chloride (CbzCl) (0.74 g; 4.35 mmol) was added thereto dropwise for 10 minutes, and stirring was performed at 5° C. for 1 hour. The ethyl acetate layer in the reaction mixture was sampled and analyzed by GC, and the reaction was finished after confirming that the peak derived from (R)—N-(3-chloropropyl)alanine ethyl ester had disappeared (each peak in GC was: (R)—N-(3-chloropropyl)alanine ethyl ester: 16.1 minutes, and (R)—N-(3-chloropropyl)-N-(benzyloxycarbonyl)alanine ethyl ester 6: 23.6 minutes).

After the reaction was finished, the ethyl acetate layer was washed with 10 mL of 10% (w/v) aqueous potassium carbonate solution, 10 mL of 1 N hydrochloric acid, 10 mL of water, and 10 mL of saturated brine in this order. Then, ethyl acetate was evaporated at 50° C. under a reduced pressure of 60 mmHg, thereby giving (R)—N-(3-chloropropyl)-N-(benzyloxycarbonyl)alanine ethyl ester 6 in the form of a colorless oil (1.43 g; yield: nearly quantitative). The results of analysis of the resultant (R)—N-(3-chloropropyl)-N-(benzyloxycarbonyl)alanine ethyl ester 6 were as follows.

$^1$H-NMR (CDCl$_3$, 400 MHz) δ 7.45-7.30 (5H, m), 5.22-5.10 (2H, m), 4.60-4.30 (1H, m), 4.20-3.90 (2H, m), 3.80-3.52 (3H, m), 3.32-3.20 (1H, m), 2.20-1.90 (2H, m), 1.60-1.45 (3H, m), 1.30-1.10 (3H, m)

Specific rotation $[\alpha]_D^{20}$=19.8 (c 1.01, CH$_3$OH).

INDUSTRIAL APPLICABILITY

According to the present invention, an optically active N-(halopropyl)amino acid derivative can be produced industrially, inexpensively and efficiently. Thus obtained optically active N-(halopropyl)amino acid derivative is used for the synthesis of an optically active cyclic amino acid, and the like.

The invention claimed is:
1. A method for producing an optically active N-(halopropyl)amino acid derivative, comprising:
obtaining a compound represented by formula (III):

(III)

by reacting an optically active alanine ester represented by formula (I):

(I)

or a salt thereof with a halogenated propane represented by formula (II):

(II)

and
obtaining an optically active N-(halopropyl)amino acid derivative represented by formula (IV):

(IV)

by introducing R$^2$C(O) onto the nitrogen atom of the compound represented by formula (III),
wherein
X$^1$ and X$^2$ are different from each other and are atoms selected from the group consisting of a chlorine atom, a bromine atom, and an iodine atom,
X$^2$ is an atom that has an atomic number larger than the atomic number of X$^1$,
R$^1$ is a linear or branched alkyl group having 1 to 4 carbon atoms that is optionally substituted with a phenyl group or is a p-nitrophenyl group,
R$^2$ is a phenyl group, a methyl group, a tert-butyl group, a tert-butoxy group, a benzyloxy group, a methoxy group, or a 9-fluorenylmethoxy group, and
the asterisk (*) indicates an asymmetric carbon atom.
2. The method of claim 1, wherein X$^1$ is a chlorine atom and X$^2$ is a bromine atom.
3. The method of claim 1, wherein the halogenated propane represented by formula (II) is in a ratio of 1.5 to 4.5 equivalents relative to an amount of the optically active alanine ester represented by formula (I) or the salt thereof.

4. The method of claim 1, wherein in the optically active alanine ester represented by formula (I), $R^1$ is an unsubstituted linear alkyl group having 1 to 4 carbon atoms.

5. The method of claim 2, wherein the halogenated propane represented by formula (II) is in a ratio of 1.5 to 4.5 equivalents relative to an amount of the optically active alanine ester represented by formula (I) or the salt thereof.

6. The method of claim 2, wherein in the optically active alanine ester represented by formula (I), $R^1$ is an unsubstituted linear alkyl group having 1 to 4 carbon atoms.

7. The method of claim 3, wherein in the optically active alanine ester represented by formula (I), $R^1$ is an unsubstituted linear alkyl group having 1 to 4 carbon atoms.

8. The method of claim 1, wherein the halogenated propane represented by formula (II) is selected from the group consisting of 1-bromo-3-chloropropane, 1-chloro-3-iodopropane, and 1-bromo-3-iodopropane.

9. The method of claim 1, wherein the ratio of the amount of the halogenated propane represented by formula (II) to the amount of the alanine ester is from 0.5 to 10.

10. The method of claim 1, wherein the reaction is carried out in the presence of a base.

11. The method of claim 10, wherein the base is selected from the group consisting of triethylamine, diisopropylethylamine, potassium carbonate, sodium hydrogencarbonate, and sodium carbonate.

12. The method of claim 1, wherein the reaction is carried out in the presence of an iodine compound.

13. The method of claim 1, wherein the compound represented by formula (III) is selected from the group consisting of the R isomer of N-(3-chloropropyl)alanine ethyl ester, the S isomer of N-(3-chloropropyl)alanine ethyl ester, the R isomer of N-(3-bromopropyl)alanine ethyl ester, the S isomer of N-(3-bromopropyl)alanine ethyl ester, the R isomer of N-(3-chloropropyl)alanine methyl ester, the S isomer of N-(3-chloropropyl)alanine methyl ester, the R isomer of N-(3-bromopropyl)alanine methyl ester, the S isomer of N-(3-bromopropyl)alanine methyl ester, the R isomer of N-(3-chloropropyl)alanine isopropyl ester, the S isomer of N-(3-chloropropyl)alanine isopropyl ester, the R isomer of N-(3-bromopropyl)alanine isopropyl ester, the S isomer of N-(3-bromopropyl)alanine isopropyl ester, the R isomer of N-(3-chloropropyl)alanine tert-butyl ester, the S isomer of N-(3-chloropropyl)alanine tert-butyl ester, the R isomer of N-(3-bromopropyl)alanine tert-butyl ester, the S isomer of N-(3-bromopropyl)alanine tert-butyl ester, the R isomer of N-(3-chloropropyl)alanine benzyl ester, the S isomer of N-(3-chloropropyl)alanine benzyl ester, the R isomer of N-(3-bromopropyl)alanine benzyl ester, the S isomer of N-(3-bromopropyl)alanine benzyl ester, the R isomer of N-(3-chloropropyl)alanine p-nitrophenyl ester, the S isomer of N-(3-chloropropyl)alanine p-nitrophenyl ester, the R isomer of N-(3-bromopropyl)alanine p-nitrophenyl ester, and the S isomer of N-(3-bromopropyl)alanine p-nitrophenyl ester.

14. The method of claim 1, wherein the compound represented by formula (IV) is selected from the group consisting of the R isomer of N-(3-chloropropyl)-N-(tert-butoxycarbonyl)alanine ethyl ester, the S isomer of N-(3-chloropropyl)-N-(tert-butoxycarbonyl)alanine ethyl ester, the R isomer of N-(3-chloropropyl)-N-(pivaloyl)alanine ethyl ester, the S isomer of N-(3-chloropropyl)-N-(pivaloyl)alanine ethyl ester, the R isomer of N-(3-chloropropyl)-N-(benzyloxycarbonyl)alanine ethyl ester, the S isomer of N-(3-chloropropyl)-N-(benzyloxycarbonyl)alanine ethyl ester, the R isomer of N-(3-chloropropyl)-N-(benzoyl)alanine ethyl ester, the S isomer of N-(3-chloropropyl)-N-(benzoyl)alanine ethyl ester, the R isomer of N-(3-chloropropyl)-N-(methoxycarbonyl)alanine ethyl ester, the S isomer of N-(3-chloropropyl)-N-(methoxycarbonyl)alanine ethyl ester, the R isomer of N-(3-chloropropyl)-N-(9-fluorenylmethoxycarbonyl)alanine ethyl ester, the S isomer of N-(3-chloropropyl)-N-(9-fluorenylmethoxycarbonyl)alanine ethyl ester, the R isomer of N-(3-chloropropyl)-N-(acetyl)alanine ethyl ester, the S isomer of N-(3-chloropropyl)-N-(acetyl)alanine ethyl ester, the R isomer of N-(3-bromopropyl)-N-(tert-butoxycarbonyl)alanine ethyl ester, the S isomer of N-(3-bromopropyl)-N-(tert-butoxycarbonyl)alanine ethyl ester, the R isomer of N-(3-chloropropyl)-N-(tert-butoxycarbonyl)alanine methyl ester, the S isomer of N-(3-chloropropyl)-N-(tert-butoxycarbonyl)alanine methyl ester, the R isomer of N-(3-chloropropyl)-N-(tert-butoxycarbonyl)alanine isopropyl ester, the S isomer of N-(3-chloropropyl)-N-(tert-butoxycarbonyl)alanine isopropyl ester, the R isomer of N-(3-chloropropyl)-N-(tert-butoxycarbonyl)alanine tert-butyl ester, the S isomer of N-(3-chloropropyl)-N-(tert-butoxycarbonyl)alanine tert-butyl ester, the R isomer of N-(3-chloropropyl)-N-(tert-butoxycarbonyl)alanine benzyl ester, the S isomer of N-(3-chloropropyl)-N-(tert-butoxycarbonyl)alanine benzyl ester, the R isomer or S isomer of N-(3-chloropropyl)-N-(tert-butoxycarbonyl)alanine p-nitrophenyl ester, and the S isomer of N-(3-chloropropyl)-N-(tert-butoxycarbonyl)alanine p-nitrophenyl ester.

* * * * *